(12) United States Patent
Peters et al.

(10) Patent No.: US 7,893,210 B2
(45) Date of Patent: Feb. 22, 2011

(54) PROCESS FOR RENATURATION OF RECOMBINANT, DISULFIDE CONTAINING PROTEINS AT HIGH PROTEIN CONCENTRATIONS IN THE PRESENCE OF AMINES

(75) Inventors: Jörg Peters, Haan (DE); Torsten Minuth, Wuppertal (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 925 days.

(21) Appl. No.: 10/495,417

(22) PCT Filed: Nov. 12, 2002

(86) PCT No.: PCT/EP02/12607

§ 371 (c)(1),
(2), (4) Date: May 13, 2004

(87) PCT Pub. No.: WO03/044055

PCT Pub. Date: May 30, 2003

(65) Prior Publication Data

US 2005/0014933 A1    Jan. 20, 2005

(30) Foreign Application Priority Data

Nov. 22, 2001 (EP) .................................. 01127373

(51) Int. Cl.
*C07K 14/54* (2006.01)
*C07K 14/52* (2006.01)
*C07K 14/435* (2006.01)
*C07K 14/00* (2006.01)

(52) U.S. Cl. ..................... 530/351; 530/408; 530/410

(58) Field of Classification Search .................. 530/350
See application file for complete search history.

(56) References Cited

U.S. PATENT DOCUMENTS

| | | | |
|---|---|---|---|
| 5,453,363 A | | 9/1995 | Rudolph et al. |
| 5,563,057 A | | 10/1996 | Gellman et al. |
| 5,593,865 A | | 1/1997 | Rudolph et al. |
| 5,721,111 A | * | 2/1998 | Unno et al. ..................... 435/12 |
| 5,723,118 A | | 3/1998 | Sebald |
| 5,728,804 A | | 3/1998 | Sharma et al. |
| 5,756,672 A | * | 5/1998 | Builder et al. ............... 530/350 |
| 2002/0052026 A1 | * | 5/2002 | Vicik .......................... 435/69.5 |
| 2004/0018586 A1 | * | 1/2004 | Rosendahl et al. ......... 435/68.1 |

FOREIGN PATENT DOCUMENTS

| | | |
|---|---|---|
| EP | 0613499 | 9/1994 |
| EP | 1022339 | 7/2000 |
| WO | 8901046 | 2/1989 |
| WO | 9640784 | 12/1996 |
| WO | 9933988 | 7/1999 |
| WO | 0073460 | 12/2000 |
| WO | 0187925 | 11/2001 |

OTHER PUBLICATIONS

Novagen Protein Refolding Kit reference sheets 1998: 9 pages.*
De Bernardez Clark, Eliana, "Refolding of Recombinant Proteins," *Current Opinion in Biotechnology*, 9: 157-163 (1998).
Lilie, et al., "Advances in Refolding of Proteins Produced in *E. coli*," *Current Opinion in Biotechnology*, 9: 497-501 (1998).
Daugherty, et al., "Artificial Chaperone-assisted Refolding of Citrate Synthase," *J. of Biological Chemistry*, 273 (51): 33961-33971 (1998).
Rozema, et al., "Artificial Chaperone-assisted Refolding of Carbonic Anhydrase B," *J. of Biological Chemistry*, 271 (7): 3478-3487 (1996).
Creighton, et al., "On the Biosynthesis of Bovine Pancreatic Trypsin Inhibitor (BPTI): Structure, Processing, Folding and Disulphide Bond Formation of the Precursor in Vitro and in Microsomes," J. Mol. Biol, 232, 1176-1196 (1993).

* cited by examiner

*Primary Examiner*—Suzanne M Noakes
*Assistant Examiner*—Marsha M Tsay
(74) *Attorney, Agent, or Firm*—Thomas C. Blankinship

(57) ABSTRACT

A method for renaturation of proteins comprising adding to a solution of denatured, chemically modified or reduced proteins a refolding buffer containing a primary, secondary or tertiary amine. Said method has been applied, for example, to interleukin-4 and bovine pancreatic trypsin inhibitor (BPTI), which were previously (i) solubilized in the presence of guanidinium hydrochloride as chaotronic agent, and (ii) subjected to sulfitolysis.

5 Claims, No Drawings

PROCESS FOR RENATURATION OF RECOMBINANT, DISULFIDE CONTAINING PROTEINS AT HIGH PROTEIN CONCENTRATIONS IN THE PRESENCE OF AMINES

CROSS-REFERENCE TO RELATED APPLICATIONS

This application is the U.S. national stage of PCT/EP02/12607, filed on Nov.12, 2002, which claims the benefit of European Patent Application No. 01127373.7, which was filed on Nov. 22, 2001, each of which is hereby incorporated by reference in its entirety.

FIELD OF THE INVENTION

The invention concerns a process for the renaturation of recombinant, eukaryotic proteins containing disulfide bonds after expression in prokaryotes.

BACKGROUND AND PRIOR ART

In case of the production of recombinant proteins in heterologous expression systems like e.g. *Escherichia coli*, these proteins often form inactive, insoluble aggregates (so-called "retractile bodies" or "inclusion bodies"). Additionally, these inclusion bodies are contaminated by host cell components like host cell proteins, nucleic acids, endotoxins and low molecular weight contaminants. It is assumed that the formation of these inclusion bodies is a result of the very high local concentration of the heterologous protein in the cell during induction and protein biosynthesis. However, the primary amino acid sequence of the heterologous protein in question is also of great importance as well as the presence of cysteine-residues that form covalent disulfide bonds during oxidative refolding. Before these target proteins can be used, e.g. for therapeutic purposes, the inclusion bodies have to be purified and, subsequently, the three-dimensional structure has to be renatured to convert the protein into the biologically active conformation.

A commonly applied sequence of process steps involves, first, the solubilization of the inclusion bodies by the addition of high concentrations of chaotropic, denaturing agents (e.g. guanidinium hydrochloride or urea), or by the addition of strongly acidic agents like, e.g. glycine/phosphoric acid mixtures. Concurrently, intramolecular disulfide bonds present in the inclusion bodies may be either reduced chemically or cleaved by the so-called sulfitolysis procedure involving sulfite and an oxidizing agent. Secondly, the solubilized protein mixture may be further purified by either chromatographic means or filtration methods, both of which are well known procedures for those skilled in the art.

Subsequently, the linearized, monomeric protein solution in the presence of high concentrations of chaotropic agent is highly diluted in order to allow for the formation of the biologically active form. This can be performed either rapidly (by simple dilution into a large volume of refolding buffer) or slowly by diafiltration or by dialysis against the refolding buffer. Other techniques described in the literature involve the adsorption of the target protein onto a chromatographic resin and, subsequently, lowering the concentration of chaotropic agent allowing refolding to take place, or size exclusion chromatography in order to separate the protein chains thereby circumventing the tendency to form aggregates. In every case, the concentration of the chaotropic salt has to be decreased below a certained limit, which is dependent on the target protein, e.g. usually below 0.5 M guanidinium hydrochloride.

The major side reaction during refolding is the formation of insoluble aggregates, which is dependent on the local concentration of folding intermediates. In the literature, a broad range of folding aids are described, effectively suppressing this formation of insoluble protein aggregates, like e.g. chaperone proteins, other types of proteins (e.g. bovine serum albumin), and several types of non-protein materials, including sugars and cyclic sugars, short chain alcohols like e.g. glycerol, pentanol, hexanol, enzyme substrates, synthetic polymers, detergents, and chaotropic salts (de Bernardez Clark, E (1998): Curr. Opinion Biotechnol. 9: 157-163 and citations therein; Lilie H, Schwarz E, Rudolph R (1998): Curr. Opinion Biotechnol. 9: 947-501 and citations therein; Sharma A, Karuppiah N (1998): U.S. Pat. No. 5,728,804 filed Jun. 2, 1995). A different approach has recently been published where so-called artificial chaperones are used to keep hydrophobic folding intermediates in solution (Gellmnan S, Rozema D B (1996): U.S. Pat. No. 5,563,057 filed Oct. 31, 1994). In a first step, hydrophobic folding intermediates are trapped into detergent micelles leading to a suppression of protein aggregation. The trapped folding intermediates cannot fold to the native conformation. In a second step, a "stripping agent", like e.g. different cyclodextrins or linear dextrins, are added in considerable molar excess to the remove the detergent again allowing the protein to refold into its biologically active conformation. There are several drawbacks to this approach like 1. Large molar excess of the expensive "stripping agent", 2. Protein aggregation occurring during the "stripping" phase, 3. Difficulty to remove residual detergent bound to the target protein, 4. Limitations in protein capacity and solubility of cyclodextrins and 5. Sensitivity of the artificial chaperone system with respect to process variations (limited robustness). Moreover, artificial chaperone systems are specific with respect to the target protein, the type of detergent and "stripping agent" and the experimental conditions employed. Hence, there is no generic artificial chaperone system available (Daugherty D L, Rozema D, Hanson P E, Gellman S H (1998): J. Biol. Chem. 273: 33961-33971; Rozema D, Gellman SH (1996): J. Biol. Chem. 271: 3478-3487).

Most of the above mentioned aggregation suppressors only work with a limited number of proteins. One exception is the amino acid L-arginine, which was shown to be generally applicable to a wide range of different proteins like e.g. t-PA, Fab fragments, lysozyme and other enzymes (Rudolph R, Fischer S, Mattes R (1997): Process for the activating of gene-technologically produced, heterologous, disulfide bridge-containing eukaryotic proteins after expression in prokaryotes. U.S. Pat. No. 5,593,865; Rudolph R, Pischer S, Mattes R (1995): Process for the activation of T-PA or ING after genetic expression in prokaryotes. U.S. Pat. No. 5,453,363; de Bernardez Clark, E (1998): Curr. Opinion Biotechnol. 9: 157-163 and citations therein).

L-arginine was shown for a number of proteins to be effective only in high molar excess with respect to the molarity of the protein to be refolded. The mechanism by which L-arginine suppresses the formation of protein aggregates is still unknown (Lilie H et al. (1998): Curr. Opinion Biotechnol. 9: 497-501). Moreover, L-arginine is an expensive, chiral fine chemical.

Hence, there is still a need to develop strategies for protein refolding using conventional techniques. From the state of the art, no generally useable, chemically simple and inexpensive aggregation suppressor is known, which can be applied in a commercially attractive refolding process of proteins at high concentrations of up to 0.5-1 g/L.

SUMMARY OF THE INVENTION

Starting from insoluble protein aggregates (so-called inclusion bodies) as obtained by overexpression in *Escherichia coli*, it is the task of the present invention to make available a commercially attractive route for the renaturation of proteins like, e.g., Interleukin-4 and its derivatives, at high protein concentrations employing a suitable, chemically simple and readily available aggregation suppressor. Due to its unspecificity, the aggregation suppressor(s) as described in the present invention may be applied to a wide range of different proteins.

The method described herein comprises adding a solution of denatured, chemically modified or reduced protein, into a refolding buffer containing a primary, more preferably secondary or tertiary amines having the formula

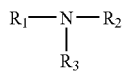

with substitutions $R_1$, $R_2$, and $R_3$, where $R_1$ and $R_2$ can be any combination of the ligands H, O=C—$NH_2$, $(CH_2)_4$—$NH_2$, $(CH_2)_3$—COOH, $(CH_2)_2$—CHOH—$CH_3$, $CH_2$—$CH_2$—OH, $CH_2$—$CH_3$, $CH_3$, $NH_2$. The residue $R_3$ can be $C(NH_2)$=NH, $C(CH_2OH)_3$, $CH_2$—$CH_2$—OH or H.

In a preferred embodiment, the refolding buffer contains a further solubility enhancer like, e.g. additional ions, like e.g. chloride or, more preferably, sulfate ions, which aid in suppressing the formation of protein aggregates synergistically.

It is known for a large number of proteins from prior art that, for renaturation, certain limiting values of protein concentration should not be exceeded. The level of these concentration limits are depending on the nature of the protein to be refolded. Now is the recognition that comparatively large amounts of denatured protein do not require larger amounts of solution volume in order to achieve larger amounts of refolded protein due to the excessively high solubilization capacity of the above mentioned amine(s) or a combination of the above mentioned amines and another solubility enhancer.

The objective of the present invention therefore include providing:

a) a method of the above kind for refolding an inactive protein into a native conformation thereby effectively suppressing the formation of protein aggregates causing loss of refolding yield and recovery of soluble protein;
b) a method of the above kind that allows the refolding at high protein concentrations; and
c) a method of the above kind that can be used with inexpensive non-chiral commodity chemicals.

These and still other objects and advantages of the present invention will be apparent from the description that follows. It should be understood that the following is merely a description of the preferred embodiments, and is not intended as a description of all possible embodiments. The claims should be looked to do determine the full scope of the invention.

Definitions

As used herein, the term "Interleukin-4 derivative" refers to muteins of human Interleukin-4 with exchanged amino acid residues at different sites of the polypeptide chain according to Sebald, W (1992): U.S. Pat. No. 5,723,118 and EP-Patent 613499B1 dated 13 Nov. 1992 and Domingues et al. (1999): PCT patent application PCT/IB00/00769.

As used herein, the term BPTI refers to bovine pancreatic trypsin inhibitor (also called aprotinin).

As used herein, "correctly folded protein" refers to the target protein in its native structure exhibiting the native disulfide bonding.

The "refolding yield", as used herein, is defined as the concentration of correctly folded, unmodified target protein (e.g., [mg/L]) in the renaturation mixture.

The "overall refolding yield", as used herein, is defined as the concentration of correctly folded, unmodified target protein (e.g., [mg/L]) divided by the amount of total protein in the renaturation mixture. The overall refolding yield is expressed in [%].

The terms "protein recovery" or "recovery of soluble protein", as used herein, refer to the ratio of soluble protein recovered after refolding and the initial total protein. The protein recovery is expressed in [%].

The term "purity" ([%]), as used herein, is calculated on the basis of the refolding yield of the target protein and the concentration of soluble protein in the renaturation mixture as determined by RP-HPLC (see example 1).

The term TRIS, as used herein, refers to the basic buffering substance Tris-(hydroxymethyl)-aminomethane. The term TEA, as used herein, refers to the basic buffering substance triethanolamine. The term GndHCl, as used herein, refers to the chaotropic salt guanidinium hydrocloride.

DETAILED DESCRIPTION OF THE PREFERRED EMBODIMENTS

The subject of the present invention is a process for the reactivation of recombinant, disulfide bridged proteins after heterologous expression in prokaryotes leading to insoluble inclusion bodies, which are, subsequent to purification of these protein aggregates, denatured in high concentrations of a suitable chaotropic salt, chemically modified (formation of a mixed disulfide between protein-SH groups and a suitable mercaptane or introduction of a sulfite group into the protein-SH groups to form S—$SO_3$ groups), and renatured in a refolding buffer using high concentrations of a primary, more preferably secondary or tertiary amines with substitutions $R_1$, $R_2$, and $R_3$, where $R_1$ and $R_2$ can be any combination of the ligands H, O=C—$NH_2$, $(CH_2)_4$—$NH_2$, $(CH_2)_3$—COOH, $(CH_2)_2$—CHOH—$CH_3$, $CH_2$—$CH_2$—OH, $CH_2$—$CH_3$, $CH_3$, $NH_2$. The residue $R_3$ can be $C(NH_2)$=NH, $C(CH_2OH)_3$, $CH_2$—$CH_2$—OH or H. Additionally, combinations with other solubility enhancers, like e.g. chloride or, more preferably, sulfate ions, are effective in preventing protein aggregation.

The production of recombinant Interleukin-4 derivative employing *Escherichia coli* as host organism has been already described in detail (Apeler H, Wehlmann H (1999) Plasmids, their construction and their use in the manufacture of Interleukin-4 and Interleukin-4 muteins. EP 10 22 339, 2000-07-26).

Methods for cell harvest, cell disruption, inclusion body purification, solubilization and chemical modification of SH-groups are well known procedures to those persons skilled in the art (Creighton T E (ed.) (1989): Protein structure—A Pratical Approach. IRL Press, Oxford, New York, Tokyo).

From prior art it is well known that chemical agents of low molecular weight may suppress the formation of aggregates during refolding. Therefore, a wide range of chemicals was screened in order to find a suitable aggregation suppressor to be employed in the refolding process of Interleukin-4 derivative, but also other proteins like, e.g., BPTI.

As indicated in example 1 (Table 1), a number of chemicals effectively aids in the solubilization of folding intermediates resulting in a significant increase of the recovery of soluble protein. However, this does not necessarily mean that these compounds also lead to a significant increase in yield of the correctly folded, biologically active disulfide isoform (see column "relative refolding yield" in Table 1). For example, the detergent cetyl triethylammonium chloride (CTAC) effectively solubilizes folding intermediates leading to an increase in protein yield of 735% compared to the phosphate control. However, CTAC fails to increase the yield of correctly folded disulfide isoform resulting in a low refolding yield and a low purity. Several agents listed in Table 1 are well known from prior art for their ability to aid as aggregation suppressor during refolding, like e.g. L-Arginine, Urea, guanidinium hydrochloride, poly(ethylene)glycols, acetamide and short chain alcohols. However, most of these failed in case of Interleukin-4 derivative with the exception of L-arginine and, to a lesser extend, guanidinium hydrochloride.

Guanidinium hydrochloride effectively solubilizes folding intermediates at optimal concentrations of 750 mM. The N-methylated or N-ethylated derivatives and bis(-1-aminoguanidinium)-sulfate are more effectively solubilizing folding intermediates at lower concentrations (200-600 mM) as compared to guanidinium hydrochloride. However, the purity of the refolded protein (18.4 to 27.1%) is much lower compared to the phosphate control.

Surprisingly, the buffer agent Tris(hydroxymethyl)-aminomethane (TRIS) in the combination with sulfuric acid at high concentrations positively affected the solubilization of folding intermediates (850%) and the refolding yield (677%) while moderately decreasing the purity compared to the phosphate control. TRIS is widely used at very low concentrations (<0.1 M) as a buffering substance in refolding mixtures, but not at high concentrations as aggregation suppressor. Ethanolamine, which is structurally related to TRIS, also positively affected the solubilization of folding intermediates (pH-titration with HCl), resulting in comparable refolding and protein yields and purities. Comparison of TRIS titrated with sulfuric acid versus hydrochloric acid shows the positive additional effect of sulfate ions on the protein yield, refolding yield and the purity. However, ethanolamine titrated with sulfuric acid did not result in synergistic effects on the refolding and protein yield.

For example, Interleukin-4 derivative and BPTI, as shown in examples 4 and 6, can be effectively refolded in a combined buffering system consisting of TRIS and sulfate ions (sulfuric acid titration). In case of Interleukin-4 derivative, protein concentrations of preferably 250 to 1000 [mg/L] can be employed, more preferably 400 to 700 [mg/L] and, even more preferably, 450 to 550 [mg/L]. L-cysteine should be included into the refolding mixture in order to allow for the formation of stabilizing disulfide bonds, preferably at 1 to 4 [mM], more preferably at 2.5 to 3.5 [mM]. TRIS/$H_2SO_4$ should be present preferably at 1 to 3 [M], more preferably at 1.4 to 2.4 [M]. The pH of the buffer is adjusted to about 7-9, more preferably 7 to 8, and most preferably 7.5.

In case of BPTI, protein concentrations of preferably 500 to 1000 [mg/L] can be employed, more preferably 600 to 800 [mg/L] and, even more preferably, 700 to 800 [mg/L]. L-cysteine should be included into the refolding mixture in order to allow for the formation of stabilizing disulfide bonds, preferably at 2.5 to 4 [mM], more preferably at 3.0 to 3.5 [mM]. TRIS/$H_2SO_4$ should be present preferably at 0.2 to 1.4 [M], more preferably at 0.3 to 1.0 [M]. The pH of the buffer is adjusted to about 7-9, more preferably 7 to 8, and most preferably 7.5.

Even more surprisingly, triethanolamine effectively solubilizes folding intermediates (800%), does not affect the purity of the refolded protein (44.1% which is' comparable to the phosphate control), resulting in the best refolding yield (1039% compared to the phosphate control).

For example, Interleukin-4 derivative, as shown in examples 5, can be effectively refolded in a combined buffering system consisting of TEA and sulfate ions (sulfuric acid titration). Protein concentrations of preferably 250 to 1000 [mg/L] can be employed, more preferably 400 to 700 [mg/L] and, even more preferably, 450 to 550 [mg/L]. L-cysteine should be included into the refolding mixture in order to allow for the formation of stabilizing disulfide bonds, preferably at 0.4 to 4 [mM], more preferably at 0.8 to 2 [mM]. TEA/$H_2SO_4$ should be present preferably at 0.5 to 2 [M], more preferably at 0.8 to 1.5 [M]. The pH of the buffer is adjusted to about 7-9, more preferably 7 to 8, and most preferably 7.5.

Taking the data listed in Table 1 together, a structure-function relationship can be deduced, revealing a general chemical principle: The most effective aggregation suppressors are primary, more preferably secondary or tertiary amines with substitutions $R_1$, $R_2$, and $R_3$, where $R_1$ and $R_2$ can be any combination of the ligands H, O=C—$NH_2$, $(CH_2)_4$—$NH_2$, $(CH_2)_3$—COOH, $(CH_2)_2$—CHOH—$CH_3$, $CH_2$—$CH_2$—OH, $CH_2$—$CH_3$, $CH_3$, $NH_2$. The residue $R_3$ can be C($NH_2$)=NH, C($CH_2OH$)$_3$, $CH_2$—$CH_2$—OH or H.

The central role of the amine function was demonstrated with canavanine-sulfate, where the central amine group is exchanged for an oxygen group, resulting in a complete loss of recovery of soluble protein (equal to the control without the addition of any aggregation suppressor) and loss of correctly refolded Interleukin-4 derivative. The data listed in Table 1 also show that the counter ion may also play a significant role. Sulfate ions are superior to chloride ions with regard to the refolding yield and inhibition of protein aggregation. Therefore, a combination of an amine as described above and a sulfate salt of sulfuric acid most effectively inhibits the formation of protein aggregates and allows the protein to refold into its native conformation.

EXAMPLE 1

Analytical Methods

Analytical RP-HPLC is carried out on a YMC C4 column (5µ, 200 Å, 4.6×250 mm) at a flow rate of 1.0 ml/min. Detection is performed at 210 nm. The optional pre-column (20 mm×4 mm) is packed with Source 15 RPC (Pharmacia, Sweden). Buffer A is 0.1% TFA, buffer B is 0.1% TFA with 70% acetonitrile. The gradient is performed as follows: 0-2 min, 40% B; 2-19.5 min, 40%-85% B; 19.5-20 min, 85%-100% B; 20-21 min, 100% B, 21-22 min, 100%-40% B, 22-25 min, 40% B (re-equilibration). Correctly folded Interleukin-4 elutes at a retention time of 16 min employing a Hewlett-Packard LC 1100 system. Correctly folded BPTI elutes at a retention time of 12.8 min. Samples of refolding mixtures are sterile filtered (0.22µ cut-off) before analysis.

The peak eluting at the retention time of the native form is integrated giving the refolding yield expressed in [mg/L] units and corresponds to the concentration of correctly folded protein (calculated based on external standard curves). The total area counts correspond to the concentration of soluble protein present in the refolding mixture expressed in [mg/L]

units. The ratio of these two values give the purity of the refolded protein expressed in [%] units.

The total protein concentration was determined after trichloroacetic acid precipitation, which was performed according to biochemical standard methods, using the commercially available BCA-assay (Pierce, USA) and bovine serum albumin (Boehringer-Mannheim, Germany) as calibration standard.

EXAMPLE 2

Preparation of Starting Materials for Refolding Experiments

Proteins were solubilized in the presence of 0.2 M Tris-HCl, pH 9 containing 8 M Guanidinium hydrochloride to give a final protein concentration of 10 [g/L]. The SH-groups were then sulfitolyzed by the addition of 30 [g/L] sodium sulfite and 60 [g/L] potassium tetrathionate. After the addition of sulfite, the solution was stirred at room temperature for 30 min in order to allow completeness of the reaction of sulfite with any disulfides present in the solubilized proteins. Subsequently, tetrathionate was added and the solution is stirred for further 90 min in order to allow the conversion of SH-groups to disulfides and the cleavage to S-sulfite-groups to run to completion. Finally, the solution was filtered through a 1.2 μ-cut off depth filter (e.g. Sartopure PP2, 1.2μ, Sartorius AG, Germany). The solution was then diafiltered against 5 volumes of diafiltration buffer consisting of 0.2 M Tris-HCl, pH 9 containing 4 M Guanidinium hydrochloride employing an ultrafiltration membrane (cut-off 10.000 MW, e.g. Hydrosart 10 kD, Sartorius AG, Germany). The retentate harvested from the ultrafiltration apparatus contained a final protein concentration of approx. 10 [g/L] and was stored at 2-8° C. for up to 2 weeks.

EXAMPLE 3

Effects of Different Chemicals on the Refolding of Interleukin-4 Derivative

The protein solution from Example 2, containing denatured, sulfitolyzed protein, is diluted into refolding buffer to give a final protein concentration of 250 [mg/L] as determined by the BCA-assay (Pierce, USA). The refolding buffer consisted of the following ingredients:

50 mM sodium phosphate buffer, pH 7.5
1 mM Ethylenediamine tetraacetic acid, tetrasodium salt (EDTA)
0.8 mM L-cysteine
A certain amount of aggregation suppressor as indicated in Table 1.

The total final volume of the refolding solution was 50 mL (glass vials, Schott, Germany). The glass vials were capped with parafilm. Refolding was allowed to run to completion within 24-36 hours with stirring on a magnetic bar stirrer (100-200 rpm). At intervals, samples were withdrawn and analyzed by RP-HPLC (see Example 1).

TABLE 1

Results of the screening for aggregation suppressors

| Group | Compound | Concentration range [mM] | Concentration optimum [mM] | Relative Refolding Yield [%] of phosphate control | Relative Protein Solubility [%] of phosphate control | Purity [%] |
|---|---|---|---|---|---|---|
| Control | Phosphate | 50 | 0 | 100 | 100 | 44.7 |
| Amino acids | L-Lysine | 0-1500 | 400 | 386 | 315 | 32.8 |
| | L-Asparagine | 0-200 | 200 | 107 | 93 | 37.8 |
| | L-Glutamine | 0-150 | 75 | 99 | 89 | 37.4 |
| | D,L-Norleucine | 0-100 | 50-100 | 106 | 93 | 37.2 |
| | L-Arginine | 0-1200 | 600 | 873 | 845 | 32.5 |
| Arginine derivatives | χ-Guanidino-butyric acid | 0-250 | 250 | 283 | 472 | 20.0 |
| | 4-Guanidino-butane-2-ol | 0-1000 | 600 | 299 | 740 | 13.8 |
| | 4-Guanidino-butylamine-sulfate | 0-1000 | 200 | 177 | 456 | 20.6 |
| | Canavanine-sulfate | 0-1200 | 600 | 0 | 100 | 0 |
| Chaotropic agents | Urea | 0-1500 | 1500 | 285 | 209 | 37.6 |
| | GuHCl | 0-1000 | 750 | 609 | 915 | 18.4 |
| | N-Methylguanidinium-sulfate | 0-1000 | 600 | 720 | 1063 | 19.9 |
| | N,N-Dimethylguanidinium-sulfate | 0-1000 | 200 | 645 | 700 | 27.1 |
| | N,N-Diethylguanidinium-sulfate | 0-1000 | 400 | 691 | 963 | 21.1 |
| | Bis-(1-Aminoguanidinium)-sulfate | 0-1000 | 400 | 798 | 1037 | 22.7 |
| Detergents | Tween 80 | 0.1-100 | 100 | 169 | 221 | 21.1 |
| | Zwittergent 3-14 | 0.01-10 | 0.01 | 85 | 76 | 30.3 |
| | Zwittergent 3-12 | 0.1-100 | 0.1 | 110 | 168 | 18.3 |
| | CHAPS | 0.5-500 | 5 | 120 | 167 | 28.9 |
| | Triton X-100 | 0.1-100 | 1 | 140 | 570 | 6.8 |
| | CTAC | 0.1-100 | 100 | 57 | 735 | 1.2 |
| Solvents | Ethanol | 1-100 | 50 | 104 | 112 | 37.1 |
| | 1-Propanol | 1-100 | 10 | 96 | 103 | 37.6 |
| | 1-Butanol | 1-100 | 5 | 102 | 107 | 38.5 |
| | 1-Hexanol | 1-100 | 1 | 88 | 80 | 44.1 |
| Salts | NaCl | 0-1000 | 800-1000 | 495 | 575 | 41.4 |
| | $NH_4Cl$ | 0-1000 | 800-1000 | 504 | 635 | 37.2 |
| | $Na_2SO_4$ | 0-1000 | 200 | 456 | 505 | 41.2 |
| | $(NH_4)_2SO_4$ | 0-1000 | 400 | 540 | 600 | 41 |

TABLE 1-continued

Results of the screening for aggregation suppressors

| Group | Compound | Concentration range [mM] | Concentration optimum [mM] | Relative Refolding Yield [%] of phosphate control | Relative Protein Solubility [%] of phosphate control | Purity [%] |
|---|---|---|---|---|---|---|
| Buffers | Phosphate | 0-1000 | 200 | 182 | 175 | 41.5 |
|  | TRIS-HCl | 0-1000 | 1000 | 489 | 505 | 24.6 |
|  | TRIS-$H_2SO_4$ | 0-1000 | 1000 | 677 | 850 | 37.8 |
|  | Ethanolamine-HCl | 0-1000 | 400 | 431 | 760 | 25.8 |
|  | Ethanolamine-$H_2SO_4$ | 200-600 | 400 | 61 | 81 | 25.7 |
|  | Triethanolamine-$H_2SO_4$ | 0-2000 | 1500 | 1039 | 800 | 44.1 |
| Others | Acetamide | 0-2000 | 800-1500 | 136 | 126 | 34.9 |
|  | PEG 200 | 0-1 | 0.5-1.0 | 102 | 89 | 38.5 |
|  | PEG 400 | 0-1 | 1.0 | 111 | 93 | 41.2 |
|  | PEG 600 | 0-1 | 0.05-0.25 | 111 | 114 | 33.1 |
|  | PEG 1000 | 0-1 | 0.25 | 101 | 89 | 38.8 |
|  | PEG 2000 | 0-1 | 0.5-1.0 | 132 | 122 | 35.2 |
|  | PEG 3000 | 0-1 | 0.1-0.5 | 122 | 104 | 35 |
|  | PEG 4000 | 0-1 | 0.1 | 153 | 133 | 37.6 |

Control:
Refolding conditions: 50 mM sodium phosphate buffer, pH 7.5, 1 mM EDTA, 0.4 mM L-cysteine, 250 mg/L total protein concentration.
Refolding yield: 8 mg/L correctly folded Interleukin-4 R121D Y124D (~3% of total protein), 23.5 mg/L recovery of soluble protein (~9% of total protein).

EXAMPLE 4

Multifactorial Optimization of the Refolding of Interleukin-4 Derivative Employing the TRIS-Sulfuric Acid Based System An attractive combination of aggregation suppressors is the TRIS-base/$H_2SO_4$-system. Therefore, this system was chosen for further optimization employing a multifactorial analysis.

The total final volume of the refolding solution was 50 mL (glass vials, Schott, Germany). The glass vials were capped with parafilm. Refolding was allowed to run to completion within 24-36 hours with stirring on a magnetic bar stirrer (100-200 rpm). At intervals, samples were withdrawn and analyzed by RP-HPLC (see Example 1).

The protein solution from Example 2, containing denatured, sulfitolyzed protein, is diluted into refolding buffer to give a final protein concentration indicated in Table 3. The following aspects of refolding buffer composition were investigated: concentration of TRIS-base (0.5 to 3 [M]), $H_2SO_4$ (depending on TRIS-concentration; 0.4 to 1.4 [M]), residual guanidinium hydrochloride concentration (80-400 mM), L-cysteine concentration (0.4 to 4 [mM]), and initial protein concentration (50 to 1000 [mg/L]). The pH of the refolding buffer was adjusted to 7.5. All refolding mixtures contained 1 mM EDTA.

The experiments described in this example was designed to allow multifactorial statistical analysis of correctly folded Interleukin-4 derivative yield data in order to assess the importance of all single factors and all two-factor interactions. A partial cubic experimental design was generated and the resulting data were also analyzed employing a partial cubic model. The coefficients of the polynoms of the partial cubic model are given in Table 2.

TABLE 2

Partial cubic model employed for the experimental design of the refolding optimization of Interleukin-4 R121D Y124D

| Term | TRIS | CYS | Protein | Term | |
|---|---|---|---|---|---|
| 0 | 0 | 0 | 0 | CONSTANT | |
| 1 | 1 | 0 | 0 | TRIS-H2SO4_[M] | Linear terms |
| 2 | 0 | 1 | 0 | Cysteine_[mM] | |
| 3 | 0 | 0 | 1 | Protein_[mg/L] | |
| 4 | 1 | 1 | 0 | TRIS-H2SO4_[M]*Cysteine_[mM] | Interaction terms |
| 5 | 1 | 0 | 1 | TRIS-H2SO4_[M]*Protein_[mg/L] | |
| 6 | 0 | 1 | 1 | Cystein_[mM]*Protein_[mg/L] | |
| 7 | 2 | 0 | 0 | TRIS-H2SO4_[M]^2 | Quadratic terms |
| 8 | 0 | 2 | 0 | Cysteine_[mM]^2 | |
| 9 | 0 | 0 | 2 | Protein_[mg/L]^2 | |
| 10 | 1 | 2 | 0 | TRIS-H2SO4_[M]*Cysteine_[mM]^2 | Partial cubic terms |
| 11 | 2 | 1 | 0 | TRIS-H2SO4_[M]^2*Cysteine_[mM] | |
| 12 | 1 | 0 | 2 | TRIS-H2SO4_[M]*Protein_[mg/L]^2 | |
| 13 | 2 | 0 | 1 | TRIS-H2SO4_[M]^2*Protein_[mg/L] | |
| 14 | 0 | 1 | 2 | Cysteine_[mM]*Protein_[mg/L]^2 | |
| 15 | 0 | 2 | 1 | Cysteine_[mM]^2*Protein_[mg/L] | |

TABLE 3

Effect of solution conditions (TRIS-H$_2$SO$_4$-system) on Interleukin-4 R121D Y124D refolding yield, recovery of soluble protein, overall refolding yield and purity

| Trial # | TRIS-base | Cysteine | Protein | Ref. Yield [mg/L] | Protein recovery [%] | Overall refolding yield [%] | Purity [%] |
|---|---|---|---|---|---|---|---|
| 1 | 3 | 4 | 50 | 9 | 81.3 | 18.00 | 22.1 |
| 2 | 3 | 0.4 | 1000 | 2.92 | 10.65 | 0.29 | 2.7 |
| 3 | 0.5 | 4 | 525 | 90.45 | 48.55 | 17.23 | 35.5 |
| 4 | 0.5 | 2.2 | 1000 | 137.7 | 46.34 | 13.77 | 29.7 |
| 5 | 1.75 | 4 | 1000 | 199.72 | 54.77 | 19.97 | 36.5 |
| 6 | 1.75 | 0.4 | 1000 | 25.05 | 27.23 | 2.50 | 9.2 |
| 7 | 3 | 2.2 | 50 | 11.3 | 60.79 | 22.60 | 37.2 |
| 8 | 0.5 | 4 | 50 | 10.37 | 53.54 | 20.73 | 38.7 |
| 9 | 3 | 0.4 | 525 | 68.32 | 55.36 | 13.01 | 23.5 |
| 10 | 0.5 | 0.4 | 525 | 81.82 | 36.66 | 15.58 | 42.5 |
| 11 | 1.75 | 0.4 | 50 | 13.6 | 62.08 | 27.21 | 43.8 |
| 12 | 0.5 | 0.4 | 1000 | 15.8 | 18.89 | 1.58 | 8.4 |
| 13 | 3 | 4 | 1000 | 176.31 | 43.94 | 17.63 | 40.1 |
| 14 | 1.75 | 4 | 525 | 131.19 | 68.94 | 24.99 | 36.2 |
| 15 | 1.3333 | 1.6 | 366.667 | 93.63 | 68.21 | 25.54 | 37.4 |
| 16 | 2.1667 | 1.6 | 366.667 | 91.95 | 69.77 | 25.08 | 35.9 |
| 17 | 3 | 2.8 | 683.333 | 134.38 | 55.72 | 19.67 | 35.3 |
| 18 | 0.5 | 1.6 | 683.333 | 110.68 | 48.94 | 16.20 | 33.1 |
| 20 | 2.1667 | 2.8 | 50 | 12.49 | 71.59 | 24.98 | 34.9 |
| 1 | 3 | 4 | 50 | 9.38 | 52.32 | 18.76 | 35.9 |
| 2 | 3 | 0.4 | 1000 | 8.94 | 18.32 | 0.89 | 4.9 |
| 3 | 0.5 | 4 | 525 | 97.16 | 50.43 | 18.51 | 36.7 |
| 4 | 0.5 | 2.2 | 1000 | 140.29 | 45.63 | 14.03 | 30.7 |
| 5 | 1.75 | 4 | 1000 | 197.53 | 56.85 | 19.75 | 34.7 |
| 6 | 1.75 | 0.4 | 1000 | 19.75 | 27.61 | 1.97 | 7.2 |
| 7 | 3 | 2.2 | 50 | 15.08 | 72.5 | 30.15 | 41.6 |

The yields obtained with selected combinations of these components are shown in Table 3. Inspection of these results shows that, under the experimental conditions employed, the following trends were apparent: (1) best refolding yields are obtained at high protein concentrations (750-1000 [mg/L]); (2) best overall refolding yields are obtained at 250 to 650 [mg/L] total protein concentration; (3) the optimal L-cysteine concentration range is 2.5 to 4 [mM]; (4) the optimal Tris-H$_2$SO$_4$-concentration range is 1.4 to 2.4 [M]; (5) best protein recovery is obtained at low protein concentrations (50 to 250 [mg/L]), high Tris-H$_2$SO$_4$-concentrations (2-3 [M]) and 2 to 3.5 [mM] L-cysteine; (6) best purity is obtained at high protein concentrations (400-1000 [mg/L]), high L-cysteine concentrations (2.5-4 [mM]). The purity is indepening on the Tris-H$_2$SO$_4$ concentration.

A compromise between optimal refolding yield, purity and protein recovery was identified employing the following settings: 500 mg/L total protein, 3.3 mM L-cysteine, 2 M Tris-H$_2$SO$_4$ and 1 mM EDTA.

Checkpoints employing these optimal conditions revealed that the predicted and measured response values fit reasonably well, indicating that the model is adequate.

| | |
|---|---|
| Overall refolding yield | Predicted: 24.9 [%] (±1.84 StdErr) |
| | Measured: 25.4 [%] (±0.37 StdErr) |
| Protein recovery | Predicted: 65.9 [%] (±6.55 StdErr) |
| | Measured: 62.9 [%] (±0.63 StdErr) |
| Purity | Predicted: 38.6 [%] (±3.63 StdErr) |
| | Measured: 40.4 [%] (±0.45 StdErr) |
| Refolding yield | Predicted: 127 [mg/L] (±14.5 StdErr) |
| | Measured: 126.9 [mg/L] (±1.85 StdErr) |

EXAMPLE 5

Multifactorial Optimization of the Refolding of Interleukin-4 Derivative Employing the Triethanolamine-Sulfuric Acid Based System Another attractive combination of aggregation suppressors is the Triethanolamine (TEA)/H$_2$SO$_4$-system. Therefore, this system was chosen for further optimization and scale-up of the protein concentration.

The total final volume of the refolding solution was 50 mL (glass vials, Schott, Germany). The glass vials were capped with parafilm. Refolding was allowed to run to completion within 24-36 hours with stirring on a magnetic bar stirrer (100-200 rpm). At intervals, samples were withdrawn and analyzed by RP-HPLC (see Example 1).

The protein solution from Example 2, containing denatured, sulfitolyzed protein, is diluted into refolding buffer to give a final protein concentration indicated in Table 5. The following aspects of refolding buffer composition were investigated: concentration of TEA (1 to 2 [M]), H$_2$SO$_4$ (depending on TEA-concentration), residual guanidinium hydrochloride concentration (80-400 mM), L-cysteine concentration (0.4 to 10 [mM]), and initial protein concentration (50 to 1000 [mg/L]). The pH of the refolding buffer was adjusted to 7.5. All refolding mixtures contained 1 mM EDTA.

The experiments described in this example was designed to allow multifactorial statistical analysis of correctly folded Interleukin-4 derivative yield data in order to assess the importance of all single factors and all two-factor interactions. A partial cubic experimental design was generated and the resulting data were also analyzed employing a partial cubic model. The coefficients of the polynoms of the partial cubic model are given in Table 4.

TABLE 4

Partial cubic model employed for the experimental design of the refolding optimization of Interleukin-4 R121D Y124D

| Term | TEA | CYS | Protein | Term | |
|---|---|---|---|---|---|
| 0 | 0 | 0 | 0 | CONSTANT | |
| 1 | 1 | 0 | 0 | TEA-H2SO4_[M] | Linear terms |
| 2 | 0 | 1 | 0 | Cysteine_[mM] | |
| 3 | 0 | 0 | 1 | Protein_[mg/L] | |
| 4 | 1 | 1 | 0 | TEA-H2SO4_[M]*Cysteine_[mM] | Interaction terms |
| 5 | 1 | 0 | 1 | TEA-H2SO4_[M]*Protein_[mg/L] | |
| 6 | 0 | 1 | 1 | Cystein_[mM]*Protein_[mg/L] | |
| 7 | 2 | 0 | 0 | TEA-H2SO4_[M]^2 | Quadratic terms |
| 8 | 0 | 2 | 0 | Cysteine_[mM]^2 | |
| 9 | 0 | 0 | 2 | Protein_[mg/L]^2 | |
| 10 | 1 | 2 | 0 | TEA-H2SO4_[M]*Cysteine_[mM]^2 | Partial cubic terms |
| 11 | 2 | 1 | 0 | TEA-H2SO4_[M]^2*Cysteine_[mM] | |
| 12 | 1 | 0 | 2 | TEA-H2SO4_[M]*Protein_[mg/L]^2 | |
| 13 | 2 | 0 | 1 | TEA-H2SO4_[M]^2*Protein_[mg/L] | |
| 14 | 0 | 1 | 2 | Cysteine_[mM]*Protein_[mg/L]^2 | |
| 15 | 0 | 2 | 1 | Cysteine_[mM]^2*Protein_[mg/L] | |

TABLE 5

Effect of solution conditions (TEA-$H_2SO_4$-system) on Interleukin-4 R121D Y124D refolding yield, recovery of soluble protein, overall refolding yield and purity

| Trial # [-] | TEA [M] | Cysteine [mM] | Protein [mg/L] | Ref. Yield [mg/L] | Protein recovery [%] | Overall refolding yield [%] | Purity [%] |
|---|---|---|---|---|---|---|---|
| 1 | 2 | 10 | 0.1 | 5.91 | 138.09 | 5.9 | 4.3 |
| 2 | 2 | 0.4 | 1 | 135.12 | 49.49 | 13.5 | 27.3 |
| 3 | 0.5 | 10 | 0.55 | 15.23 | 16.92 | 2.8 | 16.4 |
| 4 | 0.5 | 5.2 | 1 | 70.06 | 19.28 | 7 | 36.3 |
| 5 | 1.25 | 10 | 1 | 49.37 | 18.06 | 4.9 | 27.3 |
| 6 | 0.5 | 5.2 | 0.1 | 9.64 | 66.78 | 9.6 | 14.4 |
| 7 | 1.25 | 0.4 | 1 | 167.96 | 42.5 | 16.8 | 39.5 |
| 8 | 2 | 5.2 | 0.1 | 13.66 | 103.17 | 13.7 | 13.2 |
| 9 | 0.5 | 10 | 0.1 | 3.56 | 76.7 | 3.6 | 4.6 |
| 10 | 2 | 0.4 | 0.55 | 45.39 | 54.66 | 8.3 | 15.1 |
| 11 | 0.5 | 0.4 | 0.55 | 68.41 | 31.3 | 12.4 | 39.7 |
| 12 | 1.25 | 0.4 | 0.1 | 30.09 | 77.34 | 30.1 | 38.9 |
| 13 | 0.5 | 0.4 | 1 | 90.11 | 21.55 | 9 | 41.8 |
| 14 | 2 | 10 | 1 | 63.75 | 22.94 | 6.4 | 27.8 |
| 15 | 0.5 | 0.4 | 0.1 | 24.18 | 59.26 | 24.2 | 40.8 |
| 16 | 1.25 | 10 | 0.55 | 43.47 | 31.42 | 7.9 | 25.2 |
| 17 | 1 | 3.6 | 0.4 | 107.54 | 61.7 | 26.9 | 43.6 |
| 18 | 1.5 | 3.6 | 0.4 | 118.95 | 70.26 | 29.7 | 42.3 |
| 19 | 2 | 6.8 | 0.7 | 115.96 | 45.83 | 16.6 | 36.1 |
| 20 | 0.5 | 3.6 | 0.7 | 97.81 | 32.69 | 14 | 42.7 |
| 21 | 1.5 | 6.8 | 0.1 | 12.29 | 75.29 | 12.3 | 16.3 |
| 1 | 2 | 10 | 0.1 | 6.51 | 91.62 | 6.5 | 7.1 |
| 2 | 2 | 0.4 | 1 | 136.71 | 44.08 | 13.7 | 31.0 |
| 3 | 0.5 | 10 | 0.55 | 17.13 | 13.98 | 3.1 | 22.3 |
| 4 | 0.5 | 5.2 | 1 | 68.29 | 17.34 | 6.8 | 39.4 |
| 5 | 1.25 | 10 | 1 | 53.25 | 16.96 | 5.3 | 31.4 |
| 6 | 0.5 | 5.2 | 0.1 | 10.75 | 44.69 | 10.8 | 24.1 |
| 7 | 1.25 | 0.4 | 1 | 170.11 | 39.82 | 17 | 42.7 |
| 8 | 2 | 5.2 | 0.1 | 18.01 | 81.64 | 18 | 22.1 |
| 9 | 0.5 | 10 | 0.1 | 4.92 | 43.65 | 4.9 | 11.3 |

The yields obtained with selected combination of these components are shown in Table 5. Inspection of these results shows that, under the experimental conditions employed, the following trends were apparent: (1) best refolding yields are obtained at high protein concentrations (750-1000 [mg/L]); (2) best overall refolding yields are obtained at 100 to 550 [mg/L] total protein concentration; (3) the optimal L-cysteine concentration range is 0.4 to 4 [mM]; (4) the optimal TEA-$H_2SO_4$-concentration range is 1 to 1.6 [M]; (5) best protein recovery is obtained at low protein concentrations (50 to 250 [mg/L]), high TEA-$H_2SO_4$-concentrations (1.5-2 [M]) and 4 to 10 [mM] L-cysteine; (6) best purity is obtained at high protein concentrations (600-1000 [mg/L]), L-cysteine concentrations ranging between 0.4 and 4 [mM]) and at the TEA-$H_2SO_4$ concentrations ranging between 0.8 and 1:5 [M]. A compromise between optimal refolding yield, purity and protein recovery was identified employing the following settings: 500 mg/L total protein, 0.8 mM L-cysteine, 1.4 M TEA-$H_2SO_4$ and 1 mM EDTA.

Checkpoints employing these optimal conditions revealed that the predicted and measured response values fit reasonably well, indicating that the model is adequate.

| | |
|---|---|
| Overall refolding yield | Predicted: 24.6 [%] (±4.1 StdErr) |
| | Measured: 24.3 [%] (±0.8 StdErr) |
| Protein recovery | Predicted: 52.8 [%] (±10.5 StdErr) |
| | Measured: 58.2 [%] (±4.5 StdErr) |
| Purity | Predicted: 43.2 [%] (±5.3 StdErr) |
| | Measured: 41.8 [%] (±3.9 StdErr) |
| Refolding yield | Predicted: 106.8 [mg/L] (±16.9 StdErr) |
| | Measured: 121.6 [mg/L] (±2.0 StdErr) |

EXAMPLE 6

Refolding of Bovine Pancreatic Trypsin Inhibitor (BPTI, Aprotinin) Employing the TRIS-Sulfuric Acid Based System In order to demonstrate that the TRIS/$H_2SO_4$-system can also be employed for the refolding of other proteins than Interleukin-4 derivatives, the TRIS/$H_2SO_4$-system was also optimized for BPTI.

The total final volume of the refolding solution was 50 mL (glass vials, Schott, Germany). The glass vials were capped with parafilm. Refolding was allowed to run to completion within 24-36 hours with stirring on a magnetic bar stirrer (100-200 rpm). At intervals, samples were withdrawn and analyzed by RP-HPLC (see Example 1).

The protein solution from Example 2, containing denatured, sulfitolyzed protein, is diluted into refolding buffer to give a final protein concentration indicated in Table 7. The following aspects of refolding buffer composition were investigated: concentration of TRIS (0 to 2 [M]), $H_2SO_4$ (depending on the concentration of TRIS-base), residual guanidinium hydrochloride concentration (80-400 mM), L-cysteine concentration (0.1 to 4 [mM]), and initial protein concentration (50 to 1000 [mg/L]).

The pH of the refolding buffer was adjusted to 7.5. All refolding mixtures contained 1 mM EDTA.

The experiments described in this example was designed to allow multifactorial statistical analysis of correctly folded BPTI yield data in order to assess the importance of all single factors and all two-factor interactions. A partial cubic experimental design was generated and the resulting data were also analyzed employing a partial cubic model. The coefficients of the polynoms of the partial cubic model are given in Table 6.

TABLE 6

Partial Cubic model employed for the experimental design of the refolding optimization of BPTI

| Term | TRIS | CYS | Protein | Term | |
|---|---|---|---|---|---|
| 0 | 0 | 0 | 0 | CONSTANT | |
| 1 | 1 | 0 | 0 | TRIS-H2SO4_[M] | Linear terms |
| 2 | 0 | 1 | 0 | Cysteine_[mM] | |
| 3 | 0 | 0 | 1 | Protein_[mg/L] | |
| 4 | 1 | 1 | 0 | TRIS-H2SO4_[M]*Cysteine_[mM] | Interaction terms |
| 5 | 1 | 0 | 1 | TRIS-H2SO4_[M]*Protein_[mg/L] | |
| 6 | 0 | 1 | 1 | Cystein_[mM]*Protein_[mg/L] | |
| 7 | 2 | 0 | 0 | TRIS-H2SO4_[M]^2 | Quadratic terms |
| 8 | 0 | 2 | 0 | Cysteine_[mM]^2 | |
| 9 | 0 | 0 | 2 | Protein_[mg/L]^2 | |
| 10 | 1 | 2 | 0 | TRIS-H2SO4_[M]*Cysteine_[mM]^2 | |
| 11 | 2 | 1 | 0 | TRIS-H2SO4_[M]^2*Cysteine_[mM] | |
| 12 | 1 | 0 | 2 | TRIS-H2SO4_[M]*Protein_[mg/L]^2 | Partial cubic terms |
| 13 | 2 | 0 | 1 | TRIS-H2SO4_[M]^2*Protein_[mg/L] | |
| 14 | 0 | 1 | 2 | Cysteine_[mM]*Protein_[mg/L]^2 | |
| 15 | 0 | 2 | 1 | Cysteine_[mM]^2*Protein_[mg/L] | |

TABLE 7

Effect of solution conditions on BPTI refolding yield, recovery of soluble protein and overall refolding yield

| Trial # [-] | TRIS-base [M] | Cysteine [mM] | Protein [mg/L] | Ref. Yield [mg/L] | Protein recovery [%] | Overall refolding yield [%] | Purity [%] |
|---|---|---|---|---|---|---|---|
| 1 | 2 | 4 | 50 | 20.43 | 85.69 | 40.86 | 47.7 |
| 2 | 2 | 0.1 | 1000 | 0 | 0 | 0 | 0 |
| 3 | 0 | 4 | 525 | 159.29 | 61.05 | 30.34095 | 49.7 |
| 4 | 0 | 2.05 | 1000 | 275.45 | 70.84 | 27.545 | 38.9 |
| 5 | 1 | 4 | 1000 | 256.9 | 71.75 | 25.69 | 35.8 |
| 6 | 0 | 2.05 | 50 | 35.67 | 136.48 | 71.34 | 52.3 |
| 7 | 1 | 0.1 | 1000 | 0 | 2.59 | 0 | 0 |
| 8 | 2 | 2.05 | 50 | 19.45 | 80.85 | 38.9 | 48.1 |
| 9 | 0 | 4 | 50 | 8.51 | 39.92 | 17.02 | 42.6 |
| 10 | 2 | 0.1 | 525 | 0 | 0 | 0 | 0 |
| 11 | 0 | 0.1 | 525 | 0 | 0.4 | 0 | 0 |
| 12 | 1 | 0.1 | 50 | 15.71 | 69.04 | 31.42 | 45.5 |

TABLE 7-continued

Effect of solution conditions on BPTI refolding yield, recovery of soluble protein and overall refolding yield

| Trial # [-] | TRIS-base [M] | Cysteine [mM] | Protein [mg/L] | Ref. Yield [mg/L] | Protein recovery [%] | Overall refolding yield [%] | Purity [%] |
|---|---|---|---|---|---|---|---|
| 13 | 0 | 0.1 | 1000 | 0 | 1.05 | 0 | 0 |
| 14 | 2 | 4 | 1000 | 158.93 | 36.23 | 15.893 | 43.9 |
| 15 | 0 | 0.1 | 50 | 5.03 | 14.13 | 10.06 | 71.2 |
| 16 | 1 | 4 | 525 | 18.64 | 89.48 | 3.550476 | 4 |
| 17 | 0.6667 | 1.4 | 366.667 | 107.29 | 83.34 | 29.26088 | 35.1 |
| 18 | 1.3333 | 1.4 | 366.667 | 104.5 | 82.6 | 28.49997 | 34.5 |
| 19 | 2 | 2.7 | 683.333 | 97.4 | 41.66 | 14.25367 | 34.2 |
| 20 | 0 | 1.4 | 683.333 | 149.44 | 51.46 | 21.86928 | 42.5 |
| 21 | 1.3333 | 2.7 | 50 | 14.08 | 76.21 | 28.16 | 36.9 |
| 1 | 2 | 4 | 50 | 16.15 | 69.37 | 32.3 | 46.5 |
| 2 | 2 | 0.1 | 1000 | 1.47 | 3.44 | 0.147 | 4.3 |
| 3 | 0 | 4 | 525 | 162.49 | 58.91 | 30.95048 | 52.5 |
| 4 | 0 | 2.05 | 1000 | 273.77 | 68.91 | 27.377 | 39.7 |
| 5 | 1 | 4 | 1000 | 265.9 | 78.2 | 26.59 | 34 |
| 6 | 0 | 2.05 | 50 | 9.73 | 39.56 | 19.46 | 49.2 |
| 7 | 1 | 0.1 | 1000 | 0 | 0.94 | 0 | 0 |
| 8 | 2 | 2.05 | 50 | 19.18 | 77.88 | 38.36 | 49.3 |

The yields obtained with selected combination of these components are shown in Table 7. Inspection of these results shows that, under the experimental conditions employed, the following trends were apparent: (1) best refolding yields are obtained at high protein concentrations (750-1000 [mg/L]); (2) best overall refolding yields are obtained at 500 to 1000 [mg/L] total protein concentration; (3) the optimal L-cysteine concentration range is 2.5 to 4 [mM]; (4) the optimal TRIS-$H_2SO_4$-concentration range is 0.2 to 1.0 [M]; (5) best protein recovery is obtained at low protein concentrations (50 to 100 [mg/L]), moderate TRIS-$H_2SO_4$-concentrations (0.9-1.4 [M]) and 1.8 to 3.3 [mM] L-cysteine; (6) best purity is obtained at low protein concentrations (50-100 [mg/L]), L-cysteine concentrations ranging between 0.1 and 0.4 [mM]) and at the TRIS-$H_2SO_4$ concentrations ranging between 0.1 and 0.5 [M].

A compromise between optimal refolding yield, purity and protein recovery was identified employing the following settings: 700 mg/L total protein, 3.3 mM L-cysteine, 0.3 M TRIS-$H_2SO_4$ and 1 mM EDTA.

The invention claimed is:

1. A method for renaturation of Interleukin-4 or Interleukin-4 derivative comprising the step of adding a refolding buffer comprising Tris-(hydroxymethyl)-aminomethane/H2SO4 in a concentration of 1 to 3 Mol/l or triethanolamine/H2SO4 in a concentration of 0.5 to 2 Mol/l to a solution comprising denatured Interleukin-4 or denatured Interleukin-4 derivative at a protein concentration of 250 to 1000 mg/L.

2. The method of claim 1, wherein the refolding buffer further comprises contains a solubility enhancer.

3. The method of claim 2, wherein the solubility enhancer is an ion.

4. The method of claim 2, wherein the solubility enhancer is chloride.

5. The method of claim 1, wherein the denatured Interleukin-4 or denatured Interleukin-4 derivative is chemically modified or reduced.

* * * * *